(12) United States Patent
Gore et al.

(10) Patent No.: US 9,221,754 B2
(45) Date of Patent: Dec. 29, 2015

(54) CRYSTALLINE FORMS OF ZOFENOPRIL CALCIUM

(71) Applicant: Generics [UK] Limited, Hertfordshire (GB)

(72) Inventors: Vinayak Govind Gore, Maharashtra (IN); Priyesh Vijayakar, Maharashtra (IN); Ashok Pehere, Maharashtra (IN)

(73) Assignee: Generics [UK] Limited, Albany Gate, Darkes Lane, Hertfordshire (GB)

( * ) Notice: Subject to any disclaimer, the term of this patent is extended or adjusted under 35 U.S.C. 154(b) by 0 days.

(21) Appl. No.: 14/478,307

(22) Filed: Sep. 5, 2014

(65) Prior Publication Data

US 2014/0378523 A1    Dec. 25, 2014

Related U.S. Application Data

(62) Division of application No. 13/712,409, filed on Dec. 12, 2012, now Pat. No. 8,853,421, which is a division of application No. 12/867,850, filed as application No. PCT/GB2009/050199 on Feb. 26, 2009, now abandoned.

(30) Foreign Application Priority Data

Feb. 27, 2008    (IN) .............................. 354/KOL/2008

(51) Int. Cl.
*A01N 43/36* (2006.01)
*A61K 31/40* (2006.01)
*C07D 207/00* (2006.01)
*C07D 207/16* (2006.01)
*A61K 31/401* (2006.01)

(52) U.S. Cl.
CPC ............ *C07D 207/16* (2013.01); *A61K 31/401* (2013.01)

(58) Field of Classification Search
None
See application file for complete search history.

(56) References Cited

U.S. PATENT DOCUMENTS

| 4,316,906 A | 2/1982 | Ondetti et al. |
|---|---|---|
| 6,512,760 B1 | 1/2003 | Chen |
| 6,515,012 B2 | 2/2003 | Giorgi et al. |
| 6,521,760 B1 | 2/2003 | Giorgi et al. |
| 2002/0156293 A1 | 10/2002 | Giorgi et al. |
| 2005/0209288 A1 | 9/2005 | Grogan et al. |
| 2011/0098334 A1 | 4/2011 | Becker |

FOREIGN PATENT DOCUMENTS

| GB | 2028327 B | 11/1982 |
|---|---|---|
| GB | 0715626.8 | 8/2007 |
| JP | 5527199 | 2/1980 |
| JP | 2010535753 | 11/1989 |
| JP | H01287069 | 11/1989 |
| JP | 2002522417 | 7/2002 |
| WO | WO 00/07984 | 2/2000 |
| WO | WO 2007/003963 | 1/2007 |
| WO | WO 2007/138352 | 12/2007 |
| WO | WO 2009/022168 | 2/2009 |

OTHER PUBLICATIONS

Brittain (Polymorphism in Pharmaceutical Solids, vol. 95, 1999, Taylor & Francis, Harry G. Brittain (Ed.), pp. 427.
Caira, Topics in Current Chemistry, vol. 198, 1998, pp. 163-208.
Campbell Roberts et al., J. Pharm. Biomed. Anal., 28, 2002, pp. 1149-1159.
Chemical Abstracts Accession No. 1982:218225, pp. 2.
Chen et al., J. Pharm. Sci., (1999), v. 88, p. 1191.
Ganapathy, et al., Journal of the American Chemical Society, 2002, vol. 124, pp. 7821-7828.
Hurst et al., Analytica Chimica Acta, 337 (1997), 233-52.
International Search Report PCT/GB2009/050199, 7 pgs.
Joel Bernstein, "Poylmorphism in Molecular Crystals", Department of Chemistry, Table 4.6, Clarendon Press, Oxford, 2002, pp. 3.
Morissette et al. (Advanced Drug Delivery Reviews 56, 2004, pp. 275-300.
Ruben Lozano et al., "Temperature, pH and agitation rate as dissolution test discriminators of zofenopril calcium tablets", Journal of Pharmaceutical and Biomedical Analysis, 1994, vol. 12(2), pp. 173-177.
Tiwari et al., J. Pharm. Biomed. Anal., 43, 2007, pp. 865-872.
US Pharmacopia #23, National Formulary #18, 1995, pp. 1843-1844.
Written Opinion of the International Searching Authority for PCT/GB2009/050199 (10 pages).

*Primary Examiner* — Jeffrey H Murray

(57) ABSTRACT

The present invention relates to two novel crystalline forms of zofenopril calcium, to processes for their preparation and their use in pharmaceutical compositions.

17 Claims, 6 Drawing Sheets

CRYSTALLINE FORMS OF ZOFENOPRIL CALCIUM

Figure 1:
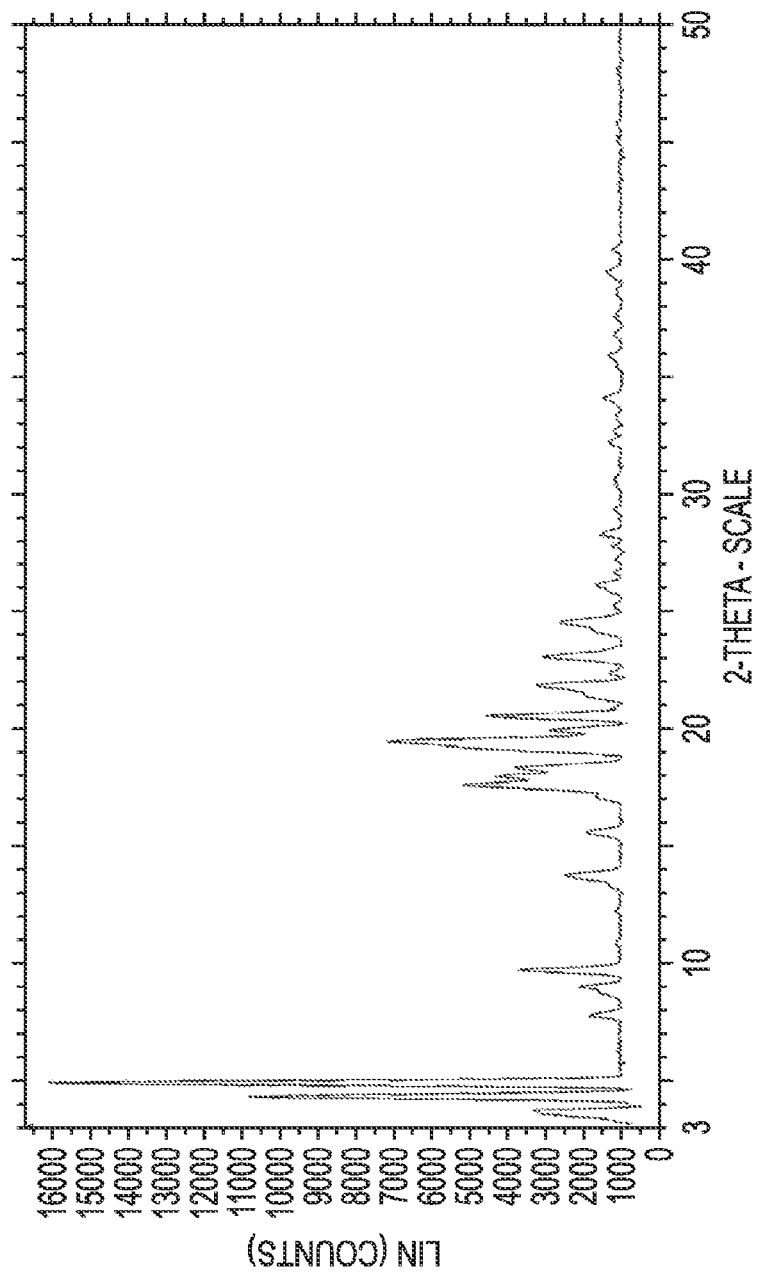

This application is a divisional of U.S. application Ser. No. 13/712,409, filed on Dec. 12, 2012, which is a divisional of U.S. application Ser. No. 12/867,850, filed on Jan. 7, 2011, which is the National Stage of PCT/GB2009/050199 filed Feb. 26, 2009, which claims foreign priority to Indian Patent Application No. 354/KOL/2008, filed on Feb. 27, 2008, all of which are incorporated by reference herein in their entirety.

FIELD OF THE INVENTION

The present invention relates to two novel crystalline forms of zofenopril calcium, to processes for their preparation and their use in pharmaceutical compositions.

BACKGROUND OF THE INVENTION

Zofenopril calcium of formula (I), chemically named (4S)-1-[(2S)-3-(benzoylthio)-2-methylpropionyl]-4-(phenylthio)-L-proline calcium salt, is a non-peptidic orally active sulphydryl ACE inhibitor with a long-lasting action and it is currently marketed for the treatment of hypertension.

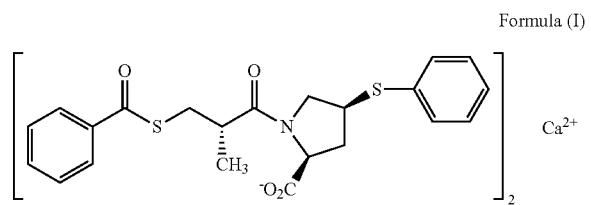

Formula (I)

The manufacturing process for many pharmaceuticals is hindered by the fact that the organic compound which is the active ingredient has handling difficulties during the manufacturing process and may impart undesirable properties to the final drug or dosage form. In addition it can be difficult to control the polymorphic form of the active pharmaceutical ingredient throughout the manufacturing process.

For pharmaceuticals in which the active ingredient can exist in more than one polymorphic form, it is particularly important to ensure that the manufacturing process for the active ingredient affords a single polymorph with a consistent level of polymorphic purity. If the process leads to a polymorph with varying degrees of polymorphic purity and/or where the process does not control polymorphic interconversion, serious problems in dissolution and/or bioavailability can result in the finished pharmaceutical composition comprising the active ingredient.

Zofenopril calcium polymorphs are disclosed in patents U.S. Pat. Nos. 6,515,012 and 4,316,906. The method for the preparation of zofenopril calcium as disclosed in U.S. Pat. No. 4,316,906 is described in U.S. Pat. No. 6,515,012 as comprising steps as follows:

(a) condensation between cis-4-(phenylthio)-L-proline and (D)-3-(benzoylthio)-2-methylpropionyl chloride in aqueous solution keeping the pH at values of 8-8.5 by addition of 5N sodium hydroxide, subsequent acidification with HCl, extraction with isobutyl acetate and concentration of the extracts, washing with saline solution, to give (4S)-1-[(2S)-3-(benzoylthio)-2-methylpropinoyl]-4-(phenylthio)-L-proline;

(b) treatment of the resinous material from the previous step in isopropanol solution with potassium 2-ethyl-hexanoate to obtain the corresponding potassium salt;

(c) dissolution of the potassium salt in water to a 57% concentration and very slow addition, with simultaneous seeding, of a slight excess of a 2N calcium chloride aqueous solution to precipitate the desired calcium salt, washing the resulting product thoroughly with water, drying under vacuum at a comparatively high temperature to give the desired calcium salt as dry powder with a melting point of about 250° C.;

(d) alternatively, (4S)-1-[(2S)-3-(benzoylthio)-2-methylpropinoyl]-4-(phenylthio)-L-proline is dissolved in ethanol and treated with the same volume of an aqueous suspension containing one equivalent of CaO; after removing ethanol and subsequently washing with ether, the aqueous suspension is freeze-dried to obtain the calcium salt with a melting point of 235-237° C.

According to U.S. Pat. No. 6,515,012, the synthesis described in U.S. Pat. No. 4,316,906 (cited above at points a, b and c) mainly yields polymorph form A, but also polymorph form B in very variable percentages and never below 20%. Moreover, the alternative synthesis described (cited at point d) affords a partially amorphous product with very variable characteristics in which form A, when present, is in concentrations much lower than those obtained in the preceding process.

U.S. Pat. Nos. 6,515,012 and 6,521,760 disclose a process for the preparation of substantially pure polymorph form A from zofenopril calcium, comprising the following steps:

(a) reaction of S(−)-3-(benzoylthio)-2-methyl-propanoic acid chloride and cis-4-(phenylthio)-L-proline in water at a pH ranging from 9.0-9.5 and recovery of zofenopril in its acidic form;

(b) salification of acid zofenopril with a potassium salt in alcoholic solution and recovery of the resulting potassium salt;

(c) conversion of the potassium salt to the calcium salt by addition of an aqueous solution of zofenopril potassium salt to a calcium chloride aqueous solution at 70-90° C. with simultaneous seeding to promote the precipitation of polymorph form A.

However, the synthesis disclosed in the aforesaid US patents for the preparation of polymorph form A has the disadvantage that the reaction is carried out at a relatively high temperature (80-85° C.) at which interconversion of the polymorphs is possible. Consequently, although substantially pure form A can be obtained from the above process, it is not very reliable and the possibility of traces of form B cannot be completely eliminated.

The aforesaid US patents also disclose a process for the preparation of polymorph form B, comprising the following steps:

(a) A solution of zofenopril potassium salt (0.27M) is sprayed in lukewarm water (55° C.), while adding a calcium chloride solution, the solution being such that the total amount of drug and calcium chloride are equimolar.

(b) The resulting suspension containing the slurry product is heated at 85° C. for 12-14 hours to obtain complete conversion to form B.

(c) After cooling at about 25° C., the product is filtered, washed with water until it is substantially free from chloride ions, and then dried under vacuum.

WO 2007/003963 discloses a process for the preparation of substantially pure polymorph form C (monohydrate form) of zofenopril calcium, comprising the following steps:

(a) reaction of S(−)-3-(benzoylthio)-2-methyl-propanoic acid chloride and cis-4-(phenylthio)-L-proline in water at a pH ranging from 9.0-9.5 and recovery of zofenopril in its acidic form;
(b) salification of acid zofenopril with a potassium salt in alcoholic solution and recovery of the resulting potassium salt;
(c) conversion of the potassium salt to the calcium salt by addition of an aqueous solution of calcium chloride dihydrate to an aqueous solution of zofenopril potassium salt at 50-55° C.

The polymorph form C described in the aforesaid WO 2007/003963 patent application has the advantage that it is prepared at milder conditions than the experimental conditions reported for the polymorphs A and B. In addition, it was found to be purer with respect to contamination by other forms (polymorph forms A and B) as indicated by XRPD data, and generally more stable to polymorphic interconversion.

However, although the properties of form C and the processes to prepare it are generally better and more convenient that those described for previous polymorphic forms, it has been observed that under certain conditions during dosage form preparation, such as micronization or wet granulation, the form C product can exhibit very slight changes in polymorphic purity. Although this difference was only to a very small extent, it could lead to variation in dissolution profile and subsequent problems in the pharmaceutical composition development.

Although formulation development may be able to circumvent the potential problems with form C, it was considered that an alternative polymorphic form with improved properties over all the known polymorphic forms may make development and manufacture more convenient and efficient and could also lead to improved pharmaceutical compositions.

OBJECT OF THE INVENTION

Therefore an object of the invention is to provide a new polymorphic form of zofenopril calcium, which is convenient to manufacture and has improved properties suitable for formulation development and a marketed pharmaceutical composition.

SUMMARY OF THE INVENTION

The present inventors have surprisingly developed two new polymorphic forms of zofenopril calcium with improved properties which circumvent the problems associated with the polymorphic forms reported in the prior art as described above.

The new polymorphic forms of zofenopril calcium have been designated as form E and form F. Both form E and form F are crystalline anhydrous forms of zofenopril calcium.

Form E and form F of zofenopril calcium are more polymorphically pure and stable than the polymorphic forms reported in the prior art. In particular, form E and form F are stable to stress conditions during dosage form preparation (see example 11).

The present inventors have also developed convenient processes for the preparation of the novel forms E and F under mild conditions.

Therefore, in a first aspect of the present invention there is provided zofenopril calcium form E characterised by an XRPD spectrum comprising at least four of the following 2θ peaks (preferably at least five, six, seven, eight, or all nine peaks): 4.2, 4.8, 9.6, 17.5, 18.0, 19.3, 19.9, 20.6 and 24.4±0.2 degrees 2θ. Preferably the zofenopril calcium form E has an XRPD spectrum substantially as shown in FIG. 1.

Figure 2:
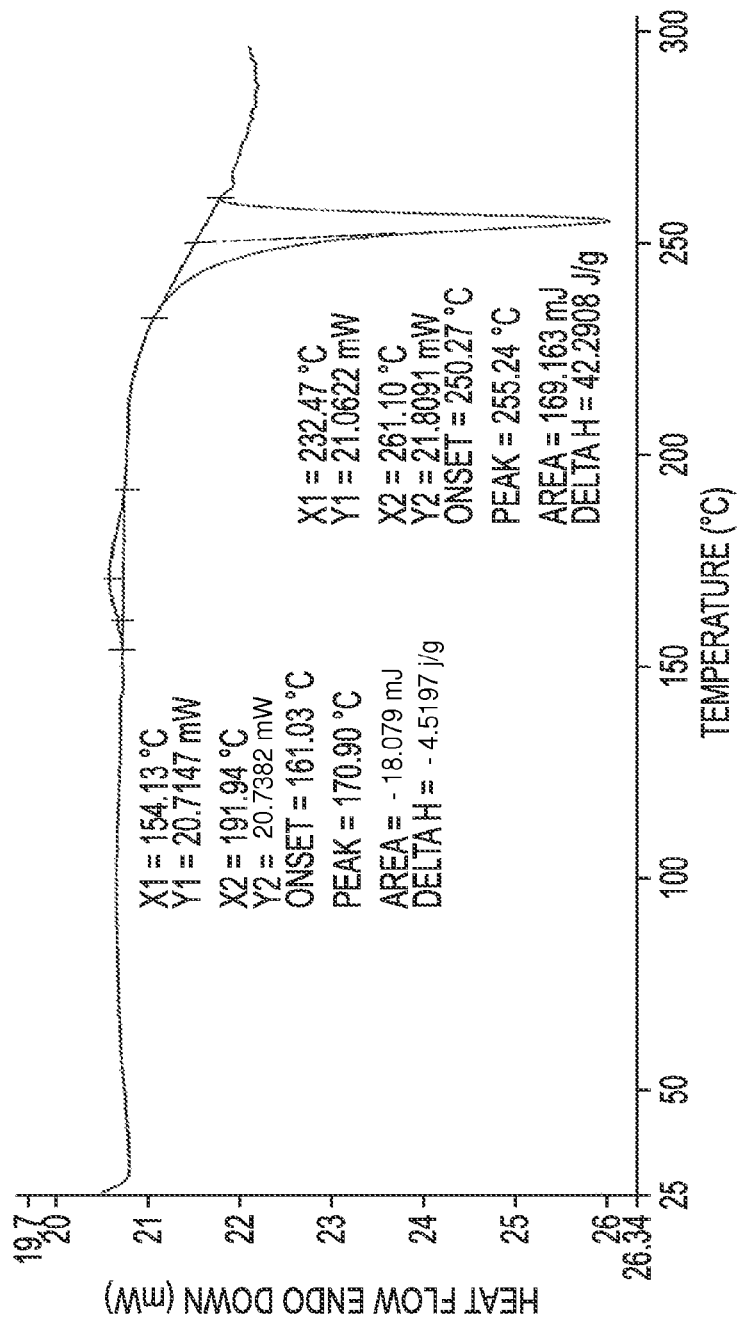

Form E may be further characterized by a differential scanning calorimetry (DSC) with an endothermic peak at about 255° C., preferably at about 255.2° C. Preferably the zofenopril calcium form E has a DSC trace substantially as shown in FIG. 2.

Figure 3:
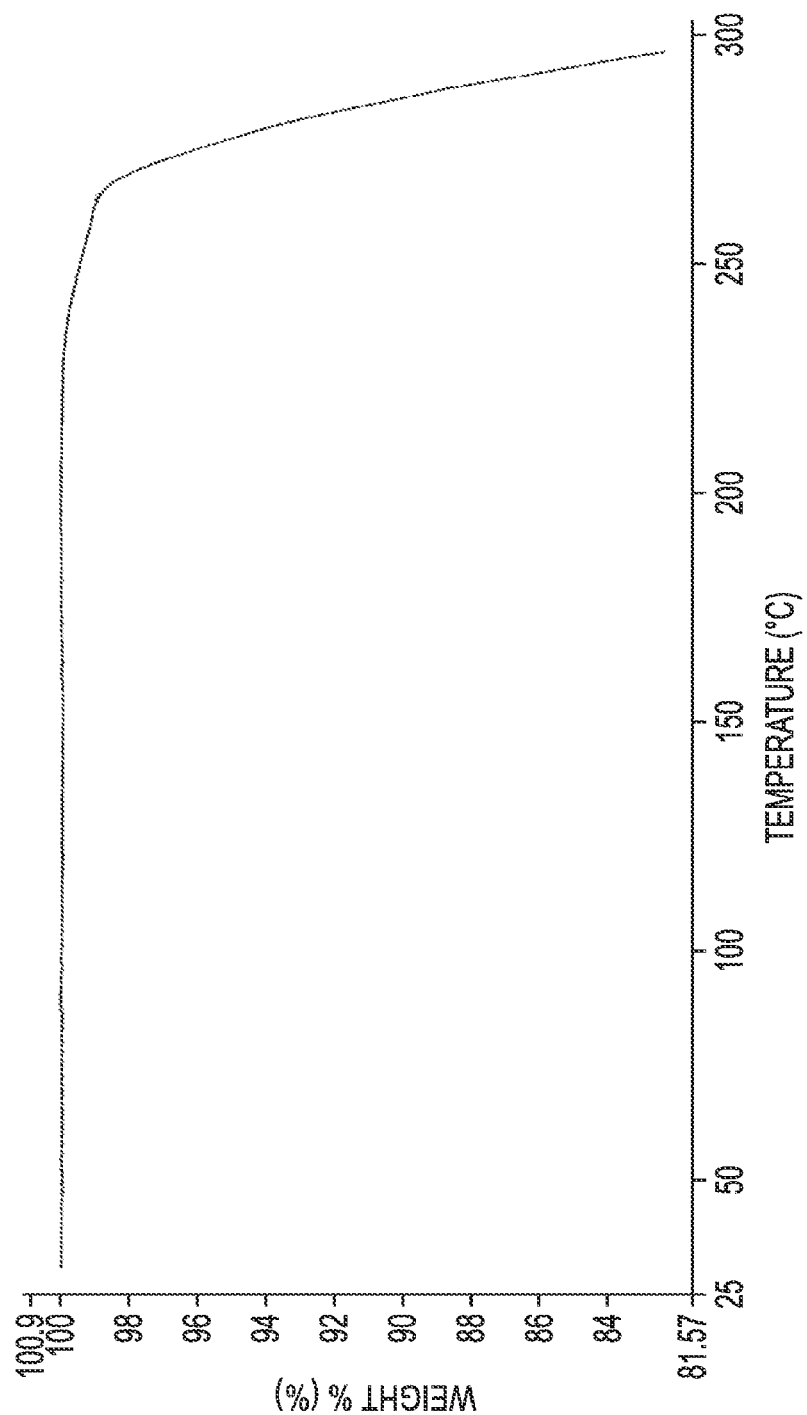

Preferably the zofenopril calcium form E has a TGA trace substantially as shown in FIG. 3.

Figure 4:
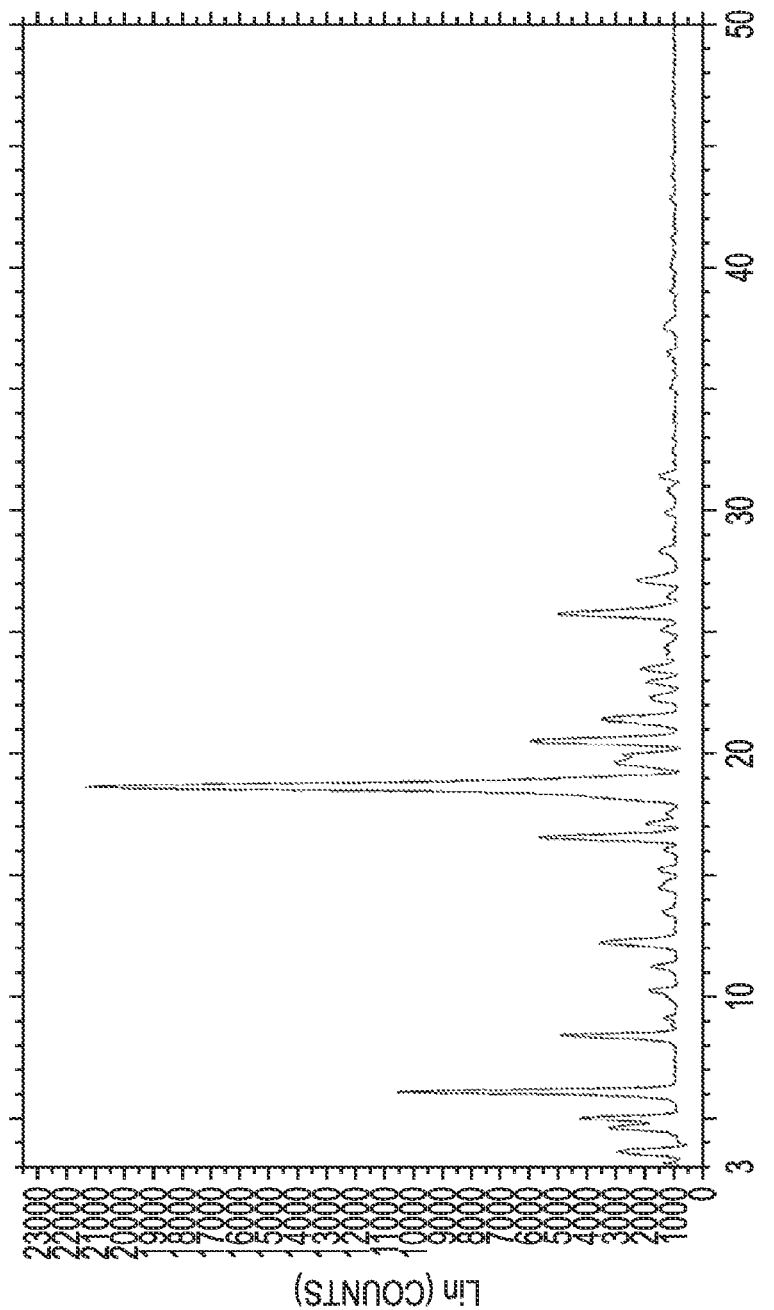

In a second aspect of the present invention there is provided zofenopril calcium form F characterised by an XRPD spectrum comprising at least four of the following 2θ peaks (preferably at least five, six, seven, eight, nine, ten, or all eleven peaks): 4.6, 6.0, 8.3, 10.2, 14.5, 16.5, 17.1, 18.2, 19.9, 21.4 and 23.5±0.2 degrees 2θ. Preferably the zofenopril calcium form F has an XRPD spectrum substantially as shown in FIG. 4.

Figure 5:
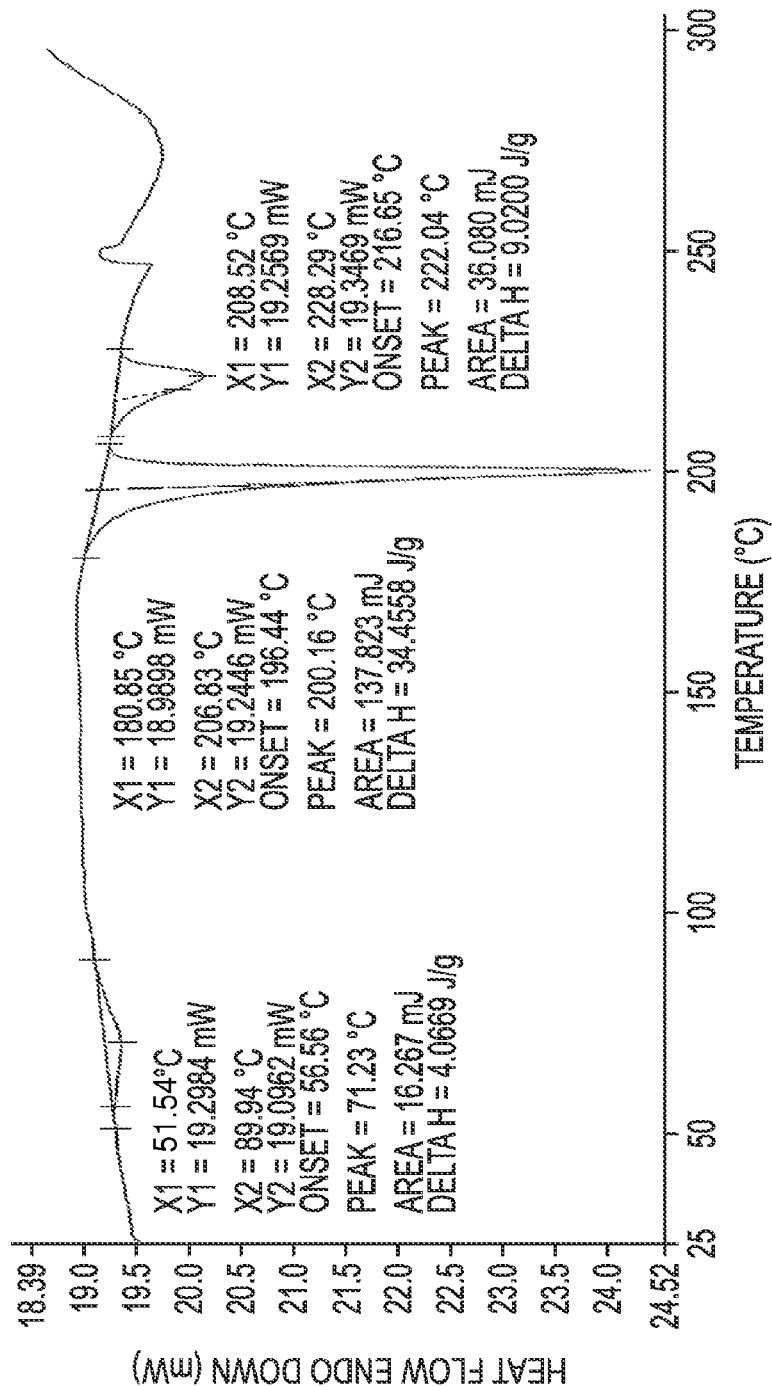

Form F may be further characterized by a differential scanning calorimetry (DSC) with an endothermic peak at about 200° C., preferably at about 200.2° C. Preferably the zofenopril calcium form F has a DSC trace substantially as shown in FIG. 5.

Figure 6:
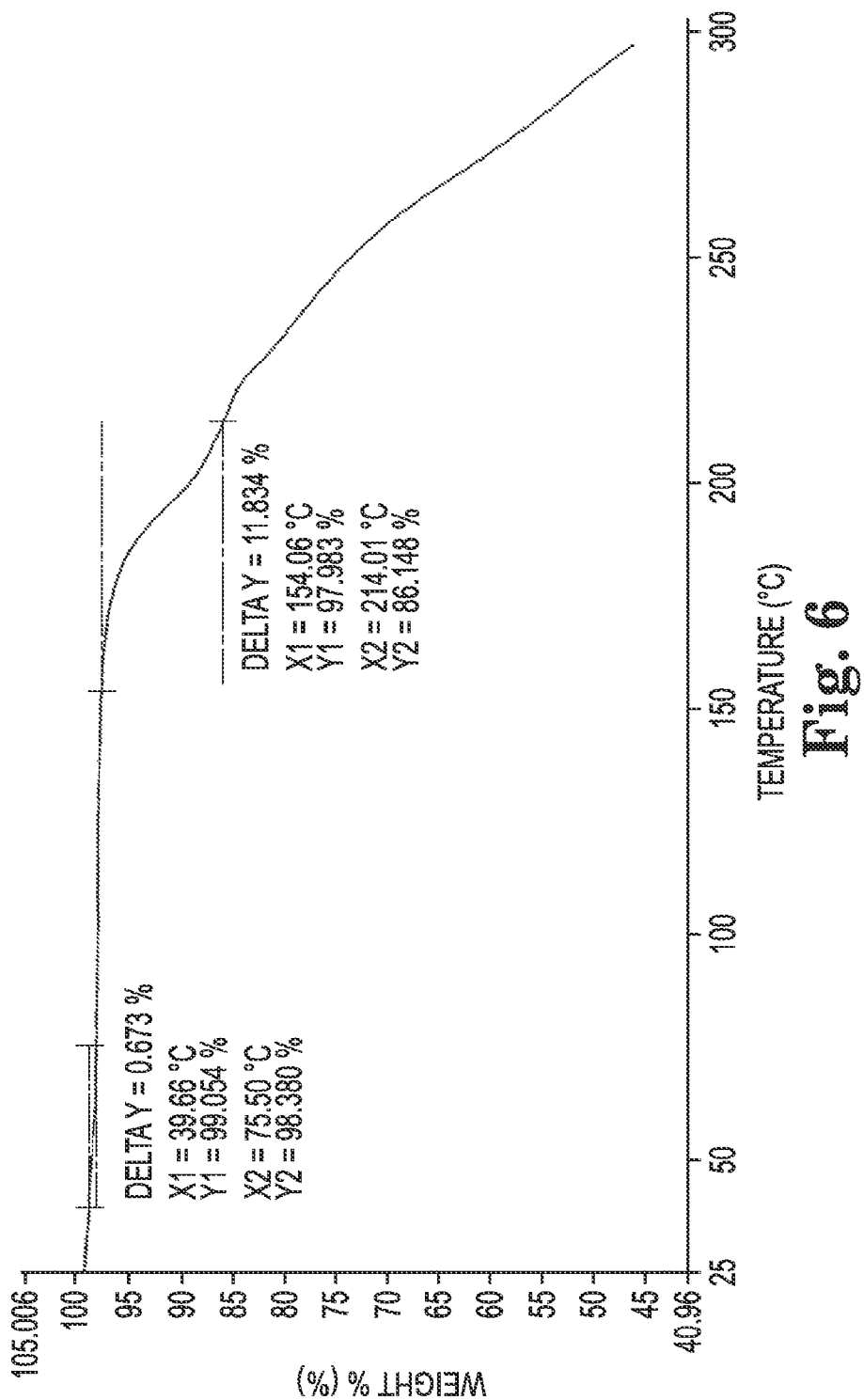

Preferably the zofenopril calcium form F has a TGA trace substantially as shown in FIG. 6.

In a third aspect of the present invention there is provided a process for preparing zofenopril calcium form E, comprising the steps of:
(a) dissolving a salt of zofenopril in a water miscible organic solvent;
(b) mixing the solution obtained in step (a) with an aqueous solution of a calcium salt; and
(c) isolating the zofenopril calcium form E; with the proviso that the salt of zofenopril in step (a) is not an amine salt.

Preferably, the water miscible organic solvent is an alcohol, an ether, a cyclic ether, a ketone or an amide.

Preferably, the water miscible organic solvent is an alcohol, such as a straight-chain, branched or cyclic $C_1$ to $C_6$ alcohol. More preferably, the alcohol is selected from methanol, ethanol, propanol, isopropanol, n-butanol or mixtures thereof.

Alternatively, the water miscible organic solvent is a cyclic ether, preferably selected from tetrahydrofuran and dioxane or mixtures thereof.

Alternatively, the water miscible organic solvent is an amide, preferably selected from N,N-dimethylformamide, formamide and N,N-dimethylacetamide or mixtures thereof.

Preferably, the zofenopril salt in step (a) is a metal salt, which is preferably selected from a potassium, sodium, lithium, calcium, magnesium or aluminium salt. Most preferably, the metal salt is a potassium salt.

Preferably, the calcium salt in step (b) is selected from the fluoride, chloride, bromide, iodide, oxide, hydroxide, carbonate, nitrate, sulfate or acetate salts. Most preferably, the calcium salt is calcium chloride.

Preferably steps (a) and (b) are carried out at a mild temperature of up to 60° C.

In a fourth aspect of the present invention there is provided a process for preparing zofenopril calcium form F, comprising the steps of:
(a) dissolving an amine salt of zofenopril in a water miscible organic solvent;
(b) mixing the solution obtained in step (a) with an aqueous solution of a calcium salt; and
(c) isolating the zofenopril calcium form F.

Preferably, the amine salt of zofenopril is selected from the dicyclohexylamine, cyclohexylamine, benzylamine, N-methylbenzylamine or α-methylbenzylamine salts. Most preferably, the amine salt is the dicyclohexylamine salt.

Preferably, the water miscible organic solvent is an alcohol, an ether, a cyclic ether, a ketone or an amide.

Preferably, the water miscible organic solvent is an alcohol, more preferably a straight-chain, branched or cyclic $C_1$ to $C_6$ alcohol. Preferably, the alcohol is selected from methanol, ethanol, propanol, isopropanol, n-butanol or mixtures thereof.

Alternatively, the water miscible organic solvent is a cyclic ether, preferably selected from tetrahydrofuran and dioxane or mixtures thereof.

Alternatively, the water miscible organic solvent is an amide, preferably selected from N,N-dimethylformamide, formamide and N,N-dimethylacetamide or mixtures thereof.

Preferably, the calcium salt in step (b) is selected from the fluoride, chloride, bromide, iodide, oxide, hydroxide, carbonate, nitrate, sulfate or acetate salts. Most preferably, the calcium salt is calcium chloride.

Preferably, steps (a) and (b) are carried out at a mild temperature of up to 60° C.

In a fifth aspect of the present invention there is provided a pharmaceutical composition comprising zofenopril calcium form E or zofenopril calcium form F. Preferably, the pharmaceutical composition according to the fifth aspect of the present invention is used to treat or prevent a disorder wherein inhibiting an angiotensin converting enzyme (ACE) is beneficial. Preferably, the disorder is selected from hypertension, cardiac decompensation, myocardial infarction, acute myocardial infarction, heart failure or chronic heart failure.

In a sixth aspect of the present invention there is provided zofenopril calcium form E comprising less than 10%, preferably less than 5%, preferably less than 1%, preferably less than 0.5%, and most preferably less than 0.1% of zofenopril calcium in other polymorphic or amorphous forms (as measured by XRPD or DSC). Preferably the zofenopril calcium form E has a chemical purity of 95%, 97%, 98%, 99%, 99.5%, 99.9% or more (as measured by HPLC).

In a seventh aspect of the present invention there is provided zofenopril calcium form F comprising less than 10%, preferably less than 5%, preferably less than 1%, preferably less than 0.5%, and most preferably less than 0.1% of zofenopril calcium in other polymorphic or amorphous forms (as measured by XRPD or DSC). Preferably the zofenopril calcium form F has a chemical purity of 95%, 97%, 98%, 99%, 99.5%, 99.9% or more (as measured by HPLC).

An eighth aspect of the present invention provides use of zofenopril calcium form E or zofenopril calcium form F, for the manufacture of a medicament for the treatment or prevention of a disorder wherein inhibiting an angiotensin converting enzyme (ACE) is beneficial. Preferably, the disorder is selected from hypertension, cardiac decompensation, myocardial infarction, acute myocardial infarction, heart failure or chronic heart failure.

A ninth aspect of the present invention provides a method of treating or preventing a disorder wherein inhibiting an angiotensin converting enzyme (ACE) is beneficial, the method comprising administering to a patient in need thereof a therapeutically or prophylactically effective amount of zofenopril calcium form E or zofenopril calcium form F. Preferably, the disorder is selected from hypertension, cardiac decompensation, myocardial infarction, acute myocardial infarction, heart failure or chronic heart failure. Preferably, the patient is a mammal, preferably a human.

BRIEF DESCRIPTION OF THE ACCOMPANYING FIGURES

FIG. 1: X-ray powder diffraction (XRPD) of zofenopril calcium form E.

FIG. 2: Differential scanning calorimetry (DSC) of zofenopril calcium form E.

FIG. 3: Thermo-gravimetric analysis (TGA) of zofenopril calcium form E.

FIG. 4: X-ray powder diffraction (XRPD) of zofenopril calcium form F.

FIG. 5: Differential scanning calorimetry (DSC) of zofenopril calcium foul F.

FIG. 6: Thermo-gravimetric analysis (TGA) of zofenopril calcium form F.

DETAILED DESCRIPTION OF THE INVENTION

The terms 'crystalline form', 'polymorphic form' and the like are used interchangeably herein.

As outlined above, the present invention provides two new crystalline forms of zofenopril calcium, form E and form F, which are non-hygroscopic, polymorphically pure and stable and have beneficial properties which avoid the problems associated with prior art forms.

The differences in XRPD data between the novel forms E and F and prior art forms of zofenopril calcium are illustrated in Table 1.

TABLE 1

| XRPD comparison [2θ values] | | | | |
|---|---|---|---|---|
| Polymorph A (WO00/07984) | Polymorph B (WO00/07984) | Polymorph C (WO07/03963) | Polymorph E | Polymorph F |
|  |  |  | 4.2 |  |
| 4.3 |  |  |  |  |
|  |  |  |  | 4.6 |
|  | 4.8 |  | 4.8 |  |
|  |  | 4.9 |  | 4.9 |
|  |  |  |  | 6.0 |
| 7.4 |  |  |  |  |
|  |  | 8.1 |  |  |
|  |  |  |  | 8.3 |
| 8.7 |  |  |  |  |
|  |  | 9.1 |  |  |
|  |  |  | 9.6 |  |
|  |  | 9.9 |  |  |
| 10.1 |  |  |  |  |
|  |  |  |  | 10.2 |
| 10.8 |  |  |  |  |
| 11.7 |  |  |  |  |
|  |  |  |  | 12.2 |
| 13.0 |  |  |  |  |
|  |  |  | 13.7 |  |
|  |  | 14.5 |  | 14.5 |
| 14.8 |  |  |  |  |
|  | 15.6 |  |  |  |
| 16.0 |  | 16.0 |  |  |
|  |  |  |  | 16.5 |
| 17.1 |  |  |  | 17.1 |
|  | 17.5 | 17.5 | 17.5 |  |
|  |  |  | 18.0 |  |
| 18.2 |  |  |  | 18.2 |
|  | 18.5 | 18.5 |  |  |
|  |  |  |  | 18.7 |
| 19.0 |  | 19.0 |  |  |
|  |  |  | 19.3 |  |
|  | 19.4 |  |  |  |
|  |  |  | 19.9 | 19.9 |
| 20.0 |  | 20.0 |  |  |
|  | 20.5 | 20.5 |  | 20.5 |
|  |  |  | 20.6 |  |
|  | 21.4 |  |  | 21.4 |
|  |  | 21.5 |  |  |
| 21.7 |  |  |  |  |
|  | 21.8 |  | 21.8 |  |
|  |  | 22.3 |  |  |
|  |  |  |  | 22.9 |
|  |  |  | 23.0 |  |

TABLE 1-continued

XRPD comparison [2θ values]

| Polymorph A (WO00/07984) | Polymorph B (WO00/07984) | Polymorph C (WO07/03963) | Polymorph E | Polymorph F |
|---|---|---|---|---|
| | 23.1 | | | |
| 23.5 | | | | 23.5 |
| | 23.9 | | | |
| | | | 24.4 | |
| | | 24.5 | | |
| 24.6 | 24.6 | | | |
| | | | | 25.7 |
| | | | | 27.1 |

In addition, convenient processes for the preparation of forms E and F have been provided by the present invention. These processes use mild conditions and low temperatures, thus minimizing the occurrence of polymorphic interconversion and producing forms E and F with very high polymorphic purity.

Preferred embodiments of the processes according to the present invention are described below.

A preferred process for the preparation of zofenopril calcium form E comprises: adding an aqueous solution of calcium chloride dihydrate to a clear water miscible organic solvent solution of zofenopril potassium salt at 25-30° C. The resulting suspension is stirred for 4 hours. The suspension is filtered at 25-30° C. and the product is washed with water until substantially free from chloride ions. The water miscible organic solvents can include alcohols (such as methanol, ethanol, propanol, isopropanol, or n-butanol), cyclic ethers (such as tetrahydrofuran or dioxane) and amides (such as N,N-dimethylformamide or N,N-dimethylacetamide). Preferably, the wet solids are dried under reduced pressure at 65° C. until the moisture content falls below 0.5%.

The XRPD pattern of the form E product thus obtained is different from the reported polymorph A, polymorph B and polymorph C of zofenopril calcium as represented in Table 1.

Polymorph E is also obtained in the case of reverse addition in the first step, when a clear solution of zofenopril potassium salt is added to a clear aqueous solution of calcium chloride dihydrate.

The temperature employed in the process for the preparation of the novel crystalline form E of zofenopril calcium is preferably from 20-60° C., and more preferably from 25-30° C.

A preferred process for the preparation of zofenopril calcium form F comprises: adding an aqueous solution of calcium chloride dihydrate to a clear water miscible organic solvent solution of zofenopril dicyclohexylamine salt at 25-30° C. The resulting suspension is stirred for 3 hours. The suspension is filtered at 25-30° C. and the product is washed with water until substantially free from chloride ions. The water miscible organic solvents can include alcohols (such as methanol, ethanol, propanol, isopropanol, or n-butanol), cyclic ethers (such as tetrahydrofuran or dioxane) and amides (such as N,N-dimethylformamide, formamide or N,N-dimethylacetamide). The wet solids are preferably dried under reduced pressure at 55° C. until the moisture content falls below 0.5%.

The product obtained, form F, exhibited a characteristic XRPD pattern and was different from the reported polymorph A, polymorph B, polymorph C and polymorph E of zofenopril calcium as represented in Table 1.

Polymorph F is also obtained in the case of reverse addition in the first step, when a clear solution of zofenopril dicyclohexylamine salt is added to a clear aqueous solution of calcium chloride dihydrate.

The temperature employed in the process for the preparation of the novel crystalline form F of zofenopril calcium is preferably from 20-60° C., and more preferably from 25-30° C.

In the processes according to the present invention, the reaction mixture is maintained at a temperature of up to 60° C. for 2 to 30 hours before filtering the suspension. Preferably, the reaction mixture is maintained at a temperature of from 50 or 55 to 60° C. for 2 to 4 hours before filtering the suspension. Alternatively, the reaction mixture is preferably maintained at a temperature of from 25 to 30° C. for 3 to 30 hours before filtering the suspension.

Preferably, the two salt solutions are mixed at a temperature of up to 60° C.

Preferably, the zofenopril calcium isolated is washed with water, preferably until substantially free from chloride ions.

Preferably, the zofenopril calcium isolated is dried, preferably under reduced pressure. Preferably, the zofenopril calcium is dried at a temperature of up to 70° C., preferably up to 60° C. Preferably, the zofenopril calcium is dried until the moisture content falls below about 1%, preferably below about 0.5%.

Preferably, the temperature throughout substantially the whole process according to the present invention is kept at 70° C. or less, preferably at 60° C. or less. For the purposes of the present invention, the temperature is kept at 70° C. or less 'throughout substantially the whole process', even if the temperature occasionally rises above 70° C., provided this rise in temperature does not influence the polymorphic form or polymorphic purity of the zofenopril calcium obtained.

The major advantage of this invention is milder experimental temperature conditions of the process to obtain the novel polymorphs and the polymorphic purity and stability of the form E and form F. The polymorphic forms of the present invention also allow zofenopril calcium to be easily purified and obtained in very high chemical purity.

The pharmaceutical composition according to the fifth aspect of the present invention can be a solution or a suspension, but is preferably a solid oral dosage form. Preferred oral dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients in accordance with the invention.

The pharmaceutical composition according to the present invention typically comprises one or more conventional pharmaceutically acceptable excipient(s) selected from the group comprising a filler, a binder, a disintegrant, a lubricant, and optionally further comprises at least one excipient selected from colouring agents, adsorbents, surfactants, film formers and plasticizers.

If the solid pharmaceutical formulation is in the form of coated tablets, the coating may be prepared from at least one film-former such as hydroxypropyl methyl cellulose, hydroxypropyl cellulose or methacrylate polymers which optionally may contain at least one plasticizer such as polyethylene glycols, dibutyl sebacate, triethyl citrate, and other pharmaceutical auxiliary substances conventional for film coatings, such as pigments and fillers.

Preferably, the pharmaceutical compositions according to the fifth aspect of the invention are for use in treating or preventing disorders where inhibiting an angiotensin converting enzyme (ACE) is beneficial. Such disorders include, but are not limited to, hypertension, cardiac decompensation, myocardial infarction, acute myocardial infarction, heart failure and chronic heart failure.

Preferably the pharmaceutical compositions according to the present invention are in unit dosage form comprising zofenopril calcium in an amount of from 1 mg to 500 mg. The unit dosage form can be administered once, twice, three times, four times or more per day. Preferably the amount of zofenopril calcium administered is from 0.1 mg to 100 mg per kg per day.

The details of the invention, its objects and advantages are illustrated below in greater detail by non-limiting examples.

EXAMPLES

Form E

The preparation of crystalline form E of zofenopril calcium is illustrated in examples 1 to 4. The products obtained exhibited identical data as depicted in FIGS. 1, 2 and 3.

Example 1

To a clear alcoholic (methanol, ethanol, propanol, isopropanol, n-butanol) solution of zofenopril potassium salt, an aqueous solution of calcium chloride dihydrate was added at 25-30° C. and the resulting suspension was stirred for 4 hours at 25-30° C. Then this suspension was filtered at 25-30° C. and the product was washed with water until free from chloride ions. The wet solids were dried under reduced pressure at 60° C. until the moisture content fell below 0.5%.
Polymorphic purity>99.9% (as measured by XRPD and DSC)
Chemical purity >99.6% (as measured by HPLC)

Example 2

To a clear aqueous solution of calcium chloride dihydrate, an alcoholic (methanol, ethanol, propanol, isopropanol, n-butanol) solution of zofenopril potassium salt was added at 25-30° C. The temperature of the reaction mixture was maintained for 4 hours at 25-30° C. Then this suspension was filtered at 25° C. and the product was washed with water until free from chloride ions. The wet solids were dried under reduced pressure at 60° C. until the moisture content fell below 0.5%.
Polymorphic purity>99.9% (as measured by XRPD and DSC)
Chemical purity>99.3% (as measured by HPLC)

Example 3

To a clear alcoholic (methanol, ethanol, propanol, isopropanol, n-butanol) solution of zofenopril potassium salt, an aqueous solution of calcium chloride dihydrate was added at 50-55° C. and the resulting suspension was stirred for 4 hours at 50-55° C. Then this suspension was filtered at 50-55° C. and the product was washed with water until free from chloride ions. The wet solids were dried under reduced pressure at 60° C. until the moisture content fell below 0.5%.
Polymorphic purity>99.9% (as measured by XRPD and DSC)
Chemical purity>99.6% (as measured by HPLC)

Example 4

To a clear aqueous solution of calcium chloride dihydrate, an alcoholic (methanol, ethanol, propanol, isopropanol, n-butanol) solution of zofenopril potassium salt was added at 50-55° C. The temperature of the reaction mixture was maintained for 4 hours at 50-55° C. Then this suspension was filtered at 50-55° C. and the product was washed with water until free from chloride ions. The wet solids were dried under reduced pressure at 60° C. until the moisture content fell below 0.5%.
Polymorphic purity>99.9% (as measured by XRPD and DSC)
Chemical purity>99.3% (as measured by HPLC)

The same crystalline form of zofenopril calcium (form E) was obtained using cyclic ethers (tetrahydrofuran, dioxane) and amides (INN-dimethylformamide, formamide, N,N-dimethylacetamide) as solvent.

Form F

The preparation of crystalline form F of zofenopril calcium is illustrated in examples 5 to 10. The products obtained exhibited identical data as depicted in FIGS. 4, 5 and 6.

Example 5

To a clear alcoholic (methanol, ethanol, propanol, isopropanol, n-butanol) solution of zofenopril dicyclohexylamine salt, an aqueous solution of calcium chloride dihydrate was added at 25-30° C. and the resulting suspension was stirred for 3 hours 25-30° C. (alcohol:water ratio 1:1). Then this suspension was filtered at 25-30° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>99.5% (as measured by HPLC)

Example 6

To a clear alcoholic (methanol, ethanol, propanol, isopropanol, n-butanol) solution of zofenopril dicyclohexylamine salt, an aqueous solution of calcium chloride dihydrate was added at 25-30° C. and the resulting suspension was stirred for 3 hours 25-30° C. (alcohol:water ratio 1:3). Then this suspension was filtered at 25-30° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>99.5% (as measured by HPLC)

Example 7

To a clear alcoholic (methanol, ethanol, propanol, isopropanol, n-butanol) solution of zofenopril dicyclohexylamine salt, an aqueous solution of calcium chloride dihydrate was added at 50-55° C. and the resulting suspension was stirred for 3 hours at 50-55° C. (alcohol:water ratio 1:1). Then this suspension was filtered at 25-30° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>99.5% (as measured by HPLC)

Example 8

To a clear aqueous solution of calcium chloride dihydrate, an alcoholic (methanol, ethanol, propanol, isopropanol, n-butanol) solution of zofenopril dicyclohexylamine salt was added at 25-30° C. and the resulting suspension was stirred for 3 hours 25-30° C. (alcohol:water ratio 1:1). Then this suspension was filtered at 25-30° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>98.5% (as measured by HPLC)

Example 9

To a clear aqueous solution of calcium chloride dihydrate, an alcoholic (methanol, ethanol, propanol, isopropanol, n-butanol) solution of zofenopril dicyclohexylamine salt was added at 25-30° C. and the resulting suspension was stirred for 3 hours 25-30° C. (alcohol:water ratio 1:3). Then this suspension was filtered at 25-30° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>98.5% (as measured by HPLC)

Example 10

To a clear aqueous solution of calcium chloride dihydrate, an alcoholic (methanol, ethanol, propanol, isopropanol, n-butanol) solution of zofenopril dicyclohexylamine salt was added at 50-55° C. and the resulting suspension was stirred for 3 hours at 50-55° C. (alcohol:water ratio 1:1). Then this suspension was filtered at 50-55° C. and the product was washed with water until free from chloride ions. The wet solids were dried under reduced pressure at 55° C. until the moisture content fell below 0.5%.
Polymorphic purity>99.9% (as measured by XRPD and DSC)
Chemical purity>98.5% (as measured by HPLC)
The same crystalline form F of zofenopril calcium was obtained using cyclic ethers (tetrahydrofuran, dioxane) and amides (N,N-dimethylformamide, formamide, N,N-dimethylacetamide) as solvent.

Example 11

Stability Studies of Polymorph Forms E and F Towards Possible Mechanical Stress Induced During Dosage Form Preparation The following studies illustrate the stability of the polymorphic forms according to the present invention to the mechanical stress that occurs during dosage formation by wet granulation.
  Polymorph E when subjected to mechanical stress during particle size reduction (milling using a multimill) retained its polymorphic composition as depicted by thermal data (XRPD, DSC and TGA). This showed that the form E is stable to mechanical stress to which the API would be subjected during dosage form (tablet) preparation.
  The stability of polymorph E was further studied by preparing its slurry in water (10% w/v) and exposing this to 50-55° C. for six hours. Thermal data (XRPD, DSC and TGA) recorded after this exposure indicated no change in polymorph E. These results suggested that the polymorph E should be stable to wet granulation.

In another stress study, a pellet of polymorph E was prepared using an Infrared spectrophotometer press machine (pressure exerted ~10 Tons). The thermal data (XRPD, DSC and TGA) of this pellet was identical to that before compression. This study also showed the stability of form E towards mechanical stress.
Similar results were seen when stress studies were conducted on form F.

It will be understood that the present invention has been described above by way of example only. The examples are not intended to limit the scope of the invention. Various modifications and embodiments can be made without departing from the scope and spirit of the invention, which is defined by the following claims only.

The invention claimed is:
1. Zofenopril calcium form F characterised by
  an XRPD spectrum comprising at least six of the following 2θ peaks: 4.6, 6.0, 8.3, 10.2, 14.5, 16.5, 17.1, 18.2, 19.9, 21.4 and 23.5±0.2 degrees 2θ.
2. Zofenopril calcium form F according to claim 1, characterised by:
  (i) an XRPD spectrum substantially as shown in FIG. 4; and/or
  (ii) a DSC trace substantially as shown in FIG. 5.
3. Zofenopril calcium form F according to claim 1, comprising less than 10% of zofenopril calcium in other polymorphic or amorphous forms.
4. Zofenopril calcium form F according to claim 1, having a differential scanning calorimetry (DSC) with an endothermic peak at about 200° C.
5. Zofenopril calcium form F according to claim 1, having a thermo-gravimetric analysis (TGA) trace substantially as shown in FIG. 6.
6. Zofenopril calcium form F according to claim 1, comprising less than 1% of zofenopril calcium in other polymorphic or amorphous forms.
7. A pharmaceutical composition comprising zofenopril calcium according to claim 1 and a pharmaceutically acceptable excipient.
8. A process for preparing zofenopril calcium form F according to claim 1, comprising the steps of:
  (a) dissolving an amine salt of zofenopril in a water miscible organic solvent;
  (b) mixing the solution obtained in step (a) with an aqueous solution of a calcium salt; and
  (c) isolating the zofenopril calcium form F.
9. The process according to claim 8, wherein the amine salt of zofenopril is
  selected from the group consisting of dicyclohexylamine, cyclohexylamine, benzylamine, N-methylbenzylamine and α-methylbenzylamine salts.
10. The process according to claim 8, wherein the water miscible organic solvent is an alcohol, an ether, a cyclic ether, a ketone or an amide.
11. The process according to claim 10, wherein the water miscible organic solvent is
  a straight-chain, branched or cyclic C1 to C6 alcohol.
12. The process according to claim 10, wherein the water miscible organic solvent is
  a cyclic ether.
13. The process according to claim 10, wherein the water miscible organic solvent is
  an amide.
14. The process according to claim 8, wherein the calcium salt in step (b) is selected from the group consisting of fluoride, chloride, bromide, iodide, oxide, hydroxide, carbonate, nitrate, sulfate, and acetate salts.

15. The process according to claim 8, wherein steps (a) and (b) are carried out at a temperature of up to 60° C.

16. A method of treating or preventing a disorder wherein inhibiting an angiotensin converting enzyme (ACE) is beneficial, the method comprising administering to a patient in need thereof a therapeutically or prophylactically effective amount of zofenopril calcium according to claim 1, wherein the disorder is selected from hypertension, cardiac decompensation, myocardial infarction, acute myocardial infarction, heart failure or chronic heart failure.

17. A method of treating or preventing a disorder wherein inhibiting an angiotensin converting enzyme (ACE) is beneficial, the method comprising administering to a patient in need thereof a therapeutically or prophylactically effective amount of a pharmaceutical composition according to claim 7, wherein the disorder is selected from hypertension, cardiac decompensation, myocardial infarction, acute myocardial infarction, heart failure or chronic heart failure.

* * * * *